(12) United States Patent
Valeij

(10) Patent No.: US 6,739,334 B2
(45) Date of Patent: May 25, 2004

(54) EXPIRATION CASSETTE THAT IS REMOVABLY INSERTABLE IN THE EXPIRATION SECTION OF A VENTILATION

(75) Inventor: Thomas Valeij, Huddinge (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/090,361

(22) Filed: Mar. 4, 2002

(65) Prior Publication Data
US 2002/0148468 A1 Oct. 17, 2002

(30) Foreign Application Priority Data
Mar. 7, 2001 (SE) .............................................. 0100757

(51) Int. Cl.$^7$ ................................................ A62B 9/04
(52) U.S. Cl. ......................... 128/202.27; 128/204.18; 128/204.22; 128/205.24; 128/204.23
(58) Field of Search ..................... 128/200.24, 203.24, 128/204.18, 204.26, 205.24, 207.12, 202.27, 202.22, 204.22, 204.23, 205.23; 600/533.538, 537, 540

(56) References Cited

U.S. PATENT DOCUMENTS

| | | | | |
|---|---|---|---|---|
| 4,870,961 A | * | 10/1989 | Barnard | 128/202.27 |
| 5,063,925 A | * | 11/1991 | Frank et al. | 128/205.24 |
| 5,065,746 A | * | 11/1991 | Steen | 128/205.24 |
| 6,230,708 B1 | * | 5/2001 | Radko | 128/205.24 |
| 6,238,351 B1 | * | 5/2001 | Orr et al. | 600/532 |
| 6,312,389 B1 | * | 11/2001 | Kofoed et al. | 600/532 |
| 6,367,475 B1 | * | 4/2002 | Kofoed et al. | 128/205.23 |
| 6,397,841 B1 | * | 6/2002 | Kenyon et al. | 128/202.27 |
| 6,402,698 B1 | * | 6/2002 | Mault | 600/532 |
| 6,427,692 B1 | * | 8/2002 | Hoglund | 128/205.24 |
| 6,447,459 B1 | * | 9/2002 | Larom | 600/538 |

FOREIGN PATENT DOCUMENTS

| | | |
|---|---|---|
| EP | 0 728 493 | 8/1996 |
| EP | 0 982 043 | 1/2000 |
| WO | WO 96/11717 | 4/1996 |
| WO | WO 99/47197 | 9/1999 |

* cited by examiner

*Primary Examiner*—Weilun Lo
*Assistant Examiner*—Michael Mendoza
(74) *Attorney, Agent, or Firm*—Schiff Hardin LLP

(57) ABSTRACT

An expiration cassette is removably insertable in a receiving section of a ventilator and contains a gas passage, an expiratory valve and a flow meter. The expiratory cassette also has a locking mechanism for locking and unlocking interaction with a receiving section in the ventilator.

6 Claims, 2 Drawing Sheets

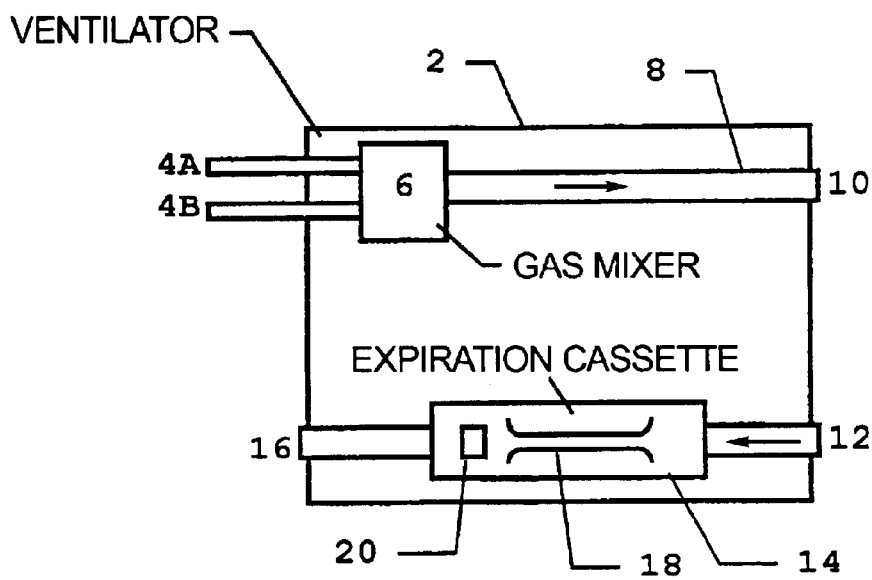
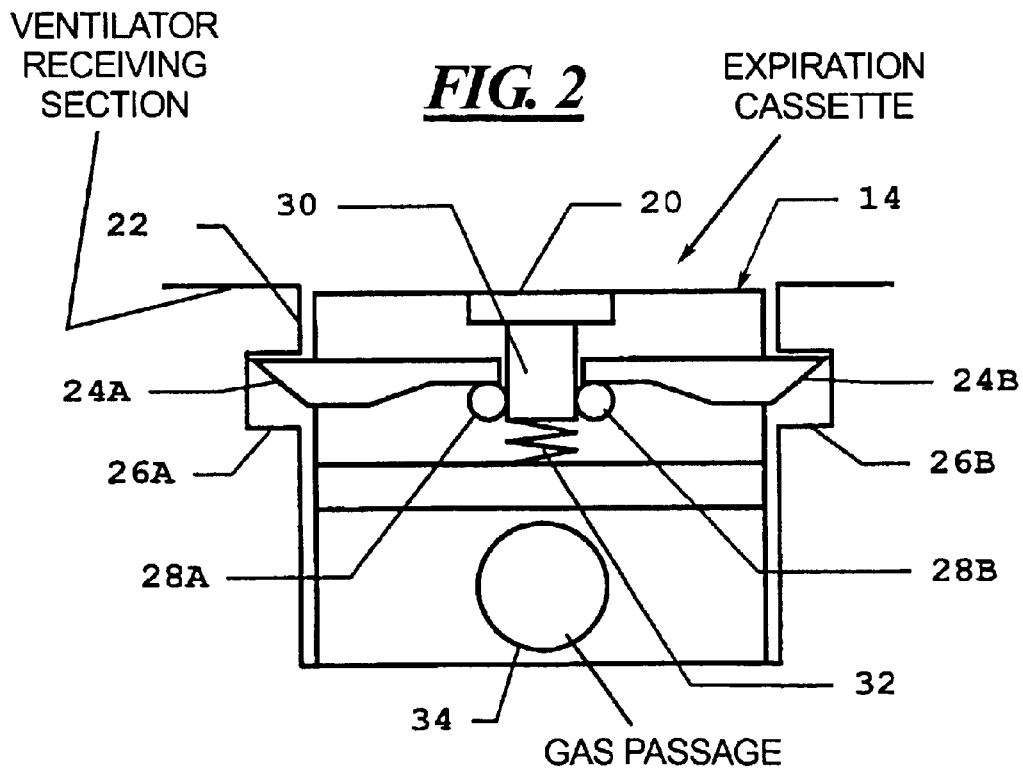

EXPIRATION CASSETTE THAT IS REMOVABLY INSERTABLE IN THE EXPIRATION SECTION OF A VENTILATION

BACKGROUND OF THE INVENTION

1. Field of the Invention

The present invention relates to an expiration cassette for a ventilator.

2. Description of the Prior Art

One problem encountered with ventilators involves their disassembly for cleaning and subsequent re-assembly. This particularly concerns the ventilators expiration section that can include an expiratory valve, a flow meter, a pressure gauge, filters etc.

A simple, sturdy device, allowing replacement of the expiratory components for cleaning in a simple operation, is therefore needed. Ensuring correct reassembly of the cleaned ventilator parts after cleaning (or of dean parts) is also important in this context.

SUMMARY OF THE INVENTION

An object of the present invention is to achieve a device which solves the above need.

The above object is achieved in accordance with the principles of the present invention in a expiration cassette that is removably insertable in a receiving section of a ventilator, the expiration cassette having a gas passage, an expiratory valve and a flow meter, and further having a locking mechanism for locking and unlocking interaction with the receiving section in the ventilator.

Placing the desired components, such as a valve, flow meter, pressure gauge etc. for the ventilator's expiration section in a cassette reduces the need for disassembly for cleaning. The entire cassette is appropriately devised for cleaning as a single unit. The cassette itself is disassembled only in exceptional instances.

Correct insertion of the cassette into the ventilator is assured with a locking mechanism that interacts with a receiving section in the ventilator.

The locking mechanism in one preferred embodiment has a pushbutton on the top of the cassette. The pushbutton can move between an open position in which the cassette can be removed from the receiving section and a closed position in which the cassette is locked into the receiving section. A spring, or the equivalent, is arranged to act on the pushbutton with a force exerted toward the locking position. The pushbutton interacts with one boss or, preferably, two bosses that are mechanically connected to the pushbutton. In the pushbutton's locked position, the bosses project beyond the outer edge of the expiration cassette. In the pushbutton's open position, the bosses are inside the outer edge of the expiration cassette. The bosses interact with openings in the receiving section to lock the cassette in place.

DESCRIPTION OF THE DRAWINGS

FIG. 1 shows a ventilator with an expiration cassette according to the invention.

FIG. 2 shows a locking mechanism in an expiration cassette interacting with a receiving section in the ventilator.

DESCRIPTION OF THE PREFERRED EMBODIMENTS

Figure 3:
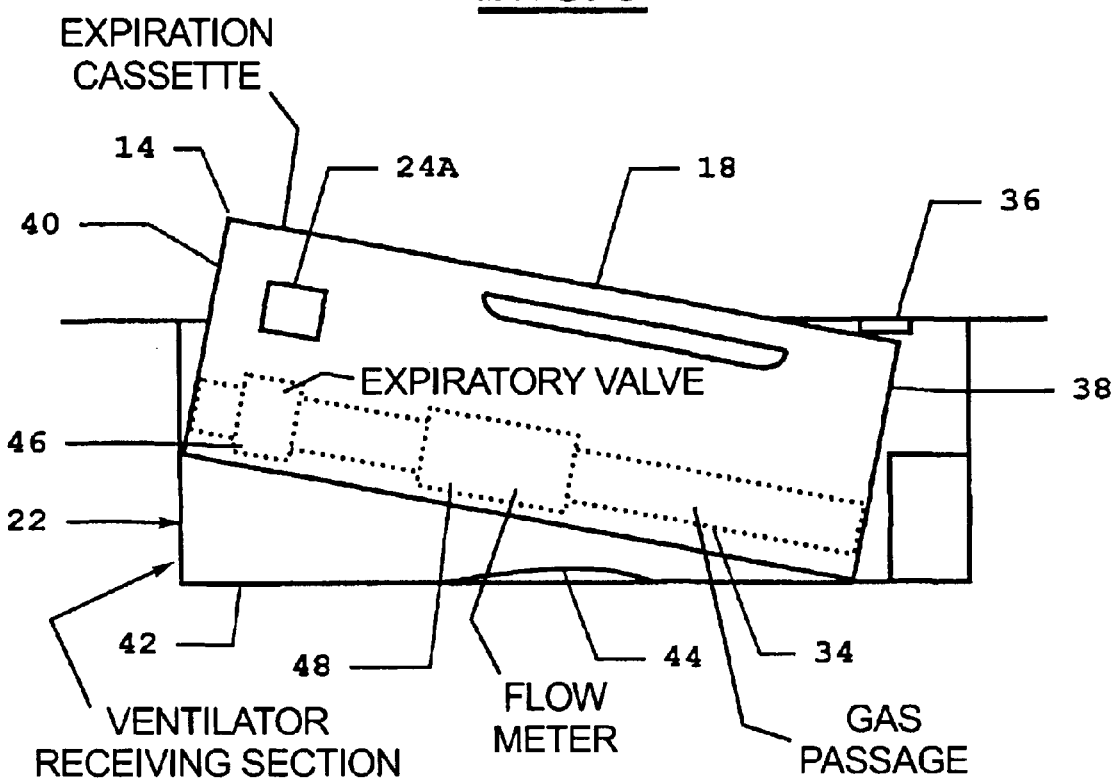
FIG. 3 shows the expiration cassette and receiving section of FIG. 2 from another angle.

FIG. 1 shows a ventilator 2 which can be connected to one or more gas sources via gas connections 4A, 4B. The gases can be regulated and mixed in a gas mixer 6 and passed through the inspiratory section 8 of the ventilator 2 to a first connection 10 for a breathing system (not shown).

It should be noted that the term 'ventilator' refers in principle to all types of apparatuses capable of providing breathing assistance, i.e. respirator, anaesthetic machines etc.

The ventilator 2 also has a second connection 12 for the breathing system, whereby gas is carried to the expiratory section of the ventilator 2 in which an expiration cassette 14 is arranged. The gas subsequently leaves the ventilator 2 through an evacuation 16.

The expiration cassette 14 is equipped with a handle 18 to facilitate handling and a pushbutton 20 for disengaging the expiratory cassette 14. The pushbutton 20 also serves as an indicator showing that the expiration cassette 14 is correctly connected to the respirator 2. This function is described in greater detail in conjunction with FIG. 2.

FIG. 2 schematically shows a locking mechanism to lock the expiration cassette 14 in a receiving section 22 in the ventilator. In addition to the pushbutton 20, the locking mechanism includes a first boss 24A and a second boss 24B that respectively interact with a first opening 26A and a second opening 26B, a first mechanical coupling 28A and a second mechanical coupling 28B, a rod 30 and a spring 32. The rod 30 is attached to the pushbutton 20 (or is an integral part of the pushbutton), and the movement of the pushbutton 20 is transmitted to the bosses 24A, 24B (whose movement is perpendicular to the direction of movement of the pushbutton 20) by the mechanical couplings 28A, 28B.

Transmission of the movement can be performed with any known mechanical transmission providing simultaneous movement of the pushbutton 20 and the bosses 24A, 24B (and vice-versa). Direct transmission is preferable; since friction-fit transmission could result in impaired functionality caused by e.g. wear etc.

A rack and pinion design has been indicated in the version shown in FIG. 2.

The spring 32 strives to force the pushbutton 20 to assume its upper position (shown in FIG. 2), i.e. the locked position.

In disassembly, the pushbutton is depressed to its lower position, i.e. the open position, whereupon the bosses 24A, 24B are retracted inside the outer edge of the expiration cassette 14, and the expiration cassette 14 can be removed.

When the expiration cassette 14 is inserted into the receiving section 22, the bosses 24A, 24B are pressed inward by the walls of the receiving section 22, whereupon the pushbutton 20 is forced down (towards its lower, open position). When the bosses 24A, 24B pass below the upper part of the openings 26A, 26B, they are forced into the openings because of the pressure of the spring 32 on the pushbutton 20. The pushbutton 20 then assumes its upper position, thereby clearly indicating that the expiration cassette has been correctly inserted.

A gas passage 34 for gas flowing through the expiration cassette 14 is also shown in FIG. 2.

FIG. 3 shows another feature of the expiration cassette 14. FIG. 3 shows the expiration cassette 14 from the side, during insertion into or removal from the receiving section 22. Here, the expiration cassette 14 is held by the handle 18.

The receiving section 22 has a stop 36 arranged to interact with the rear end 38 of the expiration cassette 14. In this instance, the locking mechanism (the boss 24A is visible) is arranged at the front end 40 of the expiration cassette 14.

The stop 36 prevents the rear end 28 of the expiration cassette 14 from being lifted out of the receiving section 22.

At the same time, the bottom 42 of the receiving section 22 is devised with a raised area 44 (exaggerated in the figure). The raised area makes it necessary for some force to be used, when the expiration cassette 14 is inserted, before the bosses 24A, 24B are able to slip into the openings. This elastic tension therefore facilitates removal of the expiration cassette 14, as its front end 40 is raised somewhat as soon as the pushbutton 20 is depressed to cause the bosses 24A, 24B to retract inside the outer edge of the expiration cassette 14.

The gas passage 34, an expiratory valve 46 and flow meter 48 contained in the cassette 14 are shown in FIG. 3.

Figure 4:
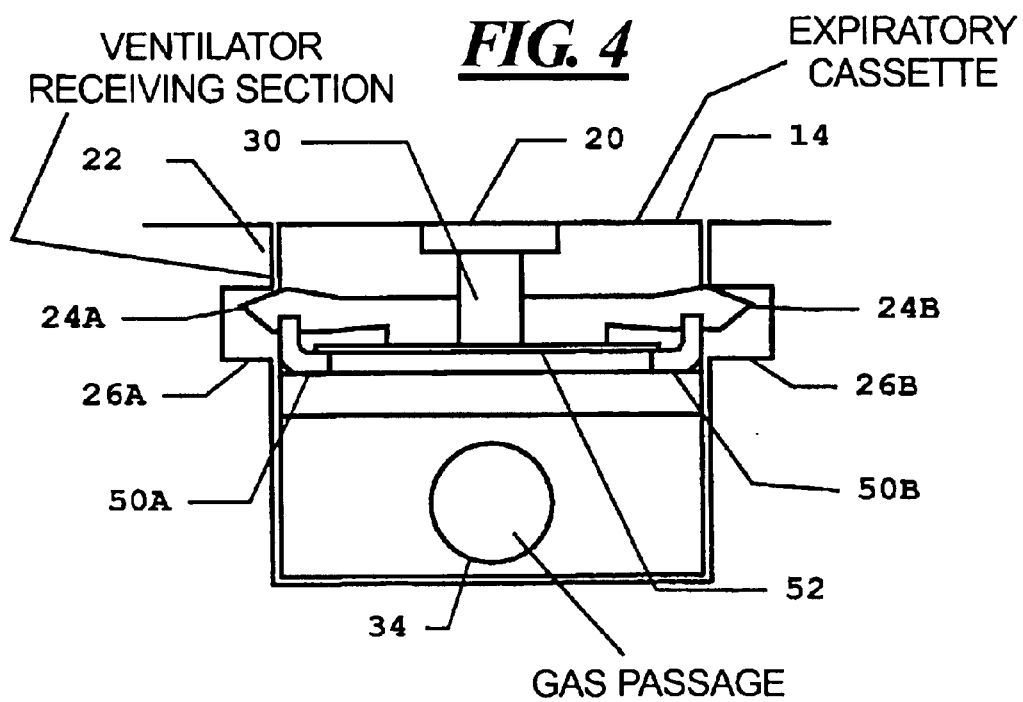
FIG. 4 shows an alternative locking mechanism in the expiration cassette of the invention.

FIG. 4 shows an alternative version of the locking mechanism in the expiration cassette 14. Components identical to those described above have the same designations. The alternative version has a pushbutton 20, a rod 30, a first boss (or piston) 24A, a second boss 24B, a first rotating body 50A, a second rotating body 50B and a leaf spring 52.

When the pushbutton 20 is depressed, the leaf spring is pushed down, and the bosses 24A, 24B are rotated with the rotating bodies 50A, 50B. The bosses 24A, 24B are accordingly moved in toward the outer edge of the expiration cassette 14, and the expiration cassette 14 can be detached.

When the expiration cassette 14 is inserted, the expiration cassette 14 is pressed down into the receiving section 22. The bosses 24A, 24B are forced out to the outer edge of the expiration cassette 14, and the pushbutton 20 is pulled down via the rotating bodies 50A, 50B and the leaf spring 52. When the expiration cassette 14 has been pushed down far enough, the bosses 24A, 24B are moved out into the openings 26A, 26B by the leaf spring's 52 resilient force, and the pushbutton 20 is lifted to indicate a locked position for the expiration cassette 14.

Other versions of the described embodiment can incorporate one boss instead of two. A single such boss can be arranged on the front of the expiration cassette. The pushbutton 20 can be arranged so it is raised in the locked position and on a level with the top of the expiration cassette in the open position. The pushbutton 20 can be replaced with a lever or the equivalent for achieving movement between two positions. Instead of having a raised area in the bottom of the receiving section, the bottom could instead be sloping or devised with spring-loaded rods that have to be depressed when an expiration cassette is connected. Alternatively, the expiration cassette can be devised with a raised area, a sloping area or an area with spring-loaded rods in order to achieve the effect of built-in elastic tension when the expiration cassette is inserted in the receiving section. As already noted, other mechanical systems for transmitting perpendicular motion can be utilized.

Although modifications and changes may be suggested by those skilled in the art, it is the intention of the inventor to embody within the patent warranted hereon all changes and modifications as reasonably and properly come within the scope of his contribution to the art.

I claim as my invention:

1. An expiration cassette comprising:
    a cassette housing containing a gas passage, an expiratory valve and a flow meter, said cassette housing being adapted to be removably inserted in a receiving section of a ventilator; and
    said cassette housing having an outer edge and a locking mechanism adapted for locking and unlocking interaction with said receiving section, said locking mechanism comprising a pushbutton disposed at a top of said cassette housing and movable between an open position and a locked position, a spring disposed to exert a force on said pushbutton in a direction urging said pushbutton toward said locked position, and at least one boss mechanically connected to said pushbutton and to said spring so that said boss, when said pushbutton is in said locked position, projects beyond said outer edge of said cassette housing and, when said pushbutton is in said open position, said boss is disposed inside of said outer edge of said cassette housing.

2. An expiration cassette as claimed in claim 1 further comprising a handle on said cassette housing adapted for gripping to move said cassette housing into and out of said receiving section.

3. A breathing assist apparatus comprising:
    a ventilator having an expiration line and a receiving section in said expiration line; and
    an expiration cassette removably inserted in said receiving section, said expiration cassette having a cassette housing containing a gas passage that is aligned with said expiration line when said expiration cassette is inserted in said receiving section, an expiratory valve and a flow meter, said cassette housing having first and second opposite ends and a locking mechanism disposed at said first end of said cassette housing for locking said expiration cassette in said receiving section and unlocking said expiration cassette from said receiving section, said second end of said cassette housing interacting with a stop in said receiving section via a non-planar contact surface, thereby requiring a counteracting force for coupling and locking said cassette housing and said receiving section together.

4. A breathing assist apparatus as claimed in claim 3 wherein said receiving section has an interior edge and wherein said cassette housing has an outer edge conforming to said interior edge of said receiving station, and wherein said locking mechanism comprising a pushbutton disposed at a top of said cassette housing and movable between an open position and a locked position, a spring disposed to exert a force on said pushbutton in a direction urging said pushbutton toward said locked position, and at least one boss mechanically connected to said pushbutton and to said spring so that said boss, when said pushbutton is in said locked position, projects beyond said outer edge of said cassette housing and, when said pushbutton is in said open position, said boss is disposed inside of said outer edge of said cassette housing.

5. A breathing assist apparatus as claimed in claim 4 wherein said receiving section has an opening, and wherein said boss is adapted to interact with said opening to lock said cassette housing in said receiving section.

6. A breathing assist apparatus as claimed in claim 3 further comprising a handle on said cassette housing adapted for gripping to move said cassette housing into and out of said receiving section.

* * * * *